US005373365A

United States Patent [19]

Brown et al.

[11] Patent Number: 5,373,365

[45] Date of Patent: Dec. 13, 1994

[54] APPARATUS AND METHOD FOR MEASURING PARTICLE CONTAMINATION

[75] Inventors: Paul T. Brown, Victor; Bruce E. Koppe, Caledonia; Robert Lewis Walton, Fairport, all of N.Y.

[73] Assignee: Eastman Kodak Company, Rochester, N.Y.

[21] Appl. No.: 995,435

[22] Filed: Dec. 23, 1992

[51] Int. Cl.[5] .............................................. G01N 21/84

[52] U.S. Cl. .................................... 356/430; 356/429; 356/431

[58] Field of Search ......................... 356/429, 430, 431

[56] References Cited

U.S. PATENT DOCUMENTS 3,588,513 6/1971 Takatsuki et al. .................. 250/219
4,019,066 4/1977 Lucas et al. .......................... 250/562
4,053,237 10/1977 Casey .................................. 356/209
4,237,539 12/1980 Piovoso et al. ..................... 356/430

*Primary Examiner*—Vincent P. McGraw
*Assistant Examiner*—LaCharles Keesee
*Attorney, Agent, or Firm*—Clyde E. Bailey

[57] ABSTRACT

An apparatus, and a method for its use, for measuring particulate contamination on a web (10) in a web-cleaning system having means for contacting and removing particles from the web (12). The means for contacting and removing particles has a particle-collecting surface (14). A light source (16) is positioned to direct a light beam against the particle-collecting surface. A sensor (18) senses the intensity of light reflected from the particle collecting surface and generates a signal $R_0$ representative of the initial reflected light intensity prior to particle collection by the particle collecting surface and a signal $R_f$ representative of the reflected light intensity after particle collection by the particle collecting surface, the difference between $R_0$ and $R_f$ being a measure of the particulate contamination level on the web.

14 Claims, 3 Drawing Sheets

TIME
26
24
ROLLER SPEED
18
WEB SPEED
$I_S$
$I_R$
$I_0$
16
14
20
12
10

18
$I_S$
20
10
16
$I_O$
22
$I_R$

18
$I_R$
12
10
16
$I_O$
20

16
10
$I_O$
12
14
18
$I_R$

APPARATUS AND METHOD FOR MEASURING PARTICLE CONTAMINATION

FIELD OF INVENTION

The present invention relates to an apparatus and method for measuring particulate contamination on a web. More particularly, it relates to an apparatus and method for monitoring an increase in particle loading on a particle transfer roller used to clean the web as a measure of the particulate contamination of the web.

BACKGROUND OF THE INVENTION

An important consideration in web manufacturing and other applications utilizing a web is the assurance of dirt-free web product. Applications such as photographic film manufacturing require cleaning and detecting particulate contamination on the web in order to minimize defects and imperfections in the web, which is important in the manufacture of products such as emulsion-coated photographic films. The detection of low level contamination is particularly important in web manufacturing applications having a fast-moving web, since the failure to detect contamination can result in having to scrap a large quantity of product.

U.S. Pat. No. 3,588,513 discloses an apparatus for photoelectric inspection of sheet materials. The apparatus comprises a light beam emitting means, for directing a light beam against the surface of the sheet material, and a means for detecting the reflection of the light from defective parts on the sheet material and for generating an electric signal corresponding to the defects of the sheet material. A disadvantage of the apparatus is that it looks directly at the sheet material and thus has a low sensitivity for measuring low levels of particulate contamination.

U.S. Pat. No. 4,019,066 discloses a method and apparatus for measuring the surface roughness of a material. The method comprises reflecting light off a moving web, measuring the reflected light, converting the collected light to electrical signals, and analyzing a direct and an alternating component of the signals to derive an index of surface roughness. Again, the apparatus has the disadvantage of looking directly at the web, rendering its sensitivity low for low level contamination. The reference also discloses that particles on the web surface having lower brightness or reflectivity can be registered by the apparatus and in certain, unspecified circumstances distort the roughness measurements.

U.S. Pat. No. 4,053,237 discloses a method of testing the surface texture of a steel chill roll. A collimated light beam is focused on the roll surface, a glossmeter is positioned on the surface, and responses are correlated to predict an expected surface texture of plastic film cast against the surface. A disadvantage is that the method applies to off-line quality testing of a roll surface texture and is unfeasible for on-line measurement of texture or contamination of a roll surface.

It is an object of the invention to provide an apparatus and method for measuring particulate contamination that is capable of measuring low levels of contamination on a web, that can be used on-line, and that is also responsive to the presence of low level contamination on a fast-moving web.

SUMMARY OF THE INVENTION

In accordance with the invention there is provided, in a web-cleaning system having means for contacting and removing particles from the web and wherein the means for contacting and removing particles has a particle-collecting surface thereon, an apparatus for measuring particulate contamination on the web comprising:

a light source positioned to direct a light beam against the particle-collecting surface;

means for sensing the intensity of light reflected from the particle collecting surface and for generating a signal $R_0$ representative of an initial reflected light intensity prior to particle collection by the particle collecting surface and a signal $R_f$ representative of a reflected light intensity after particle collection by the particle collecting surface, the difference between $R_0$ and $R_f$ being a measure of the particulate contamination level on the web; and means for indicating the difference between $R_0$ and $R_f$.

There is also provided a method of measuring particulate contamination on a web in a web-cleaning system, the web-cleaning system having means for contacting and removing particles from the web and wherein the means for contacting and removing particles has a particle-collecting surface thereon, comprising the steps of:

(a) providing a light source;

(b) providing a means for sensing light intensity and for generating a signal representative of the sensed light intensity;

(c) positioning the light source to direct light therefrom against the particle-collecting surface;

(d) sensing an initial intensity of light reflected from the particle-collecting surface prior to transferring particles from the web to the particle-collecting surface and generating a signal $R_0$ representative of the initial intensity;

(e) contacting the web with the particle-collecting surface to transfer particles from the web to the particle-collecting surface;

(f) sensing a final intensity of light reflected from the particle-collecting surface after transferring particles from the web to the particle-collecting surface and generating a signal $R_f$ representative of the final intensity;

(g) comparing $R_f$ to $R_0$ to obtain a measure of the particulate contamination on the web.

The invention provides an apparatus and method having improved sensitivity for sensing particulate contamination on a web. The invention can detect low levels of particulate contamination on the web and can be used on-line to provide real-time feedback on web contamination levels. The invention can detect the existence of low contamination levels on a fast-moving web, and can be useful in identifying a contaminant and the source of a contamination.

DESCRIPTION OF THE PREFERRED EMBODIMENTS

Figure 1:
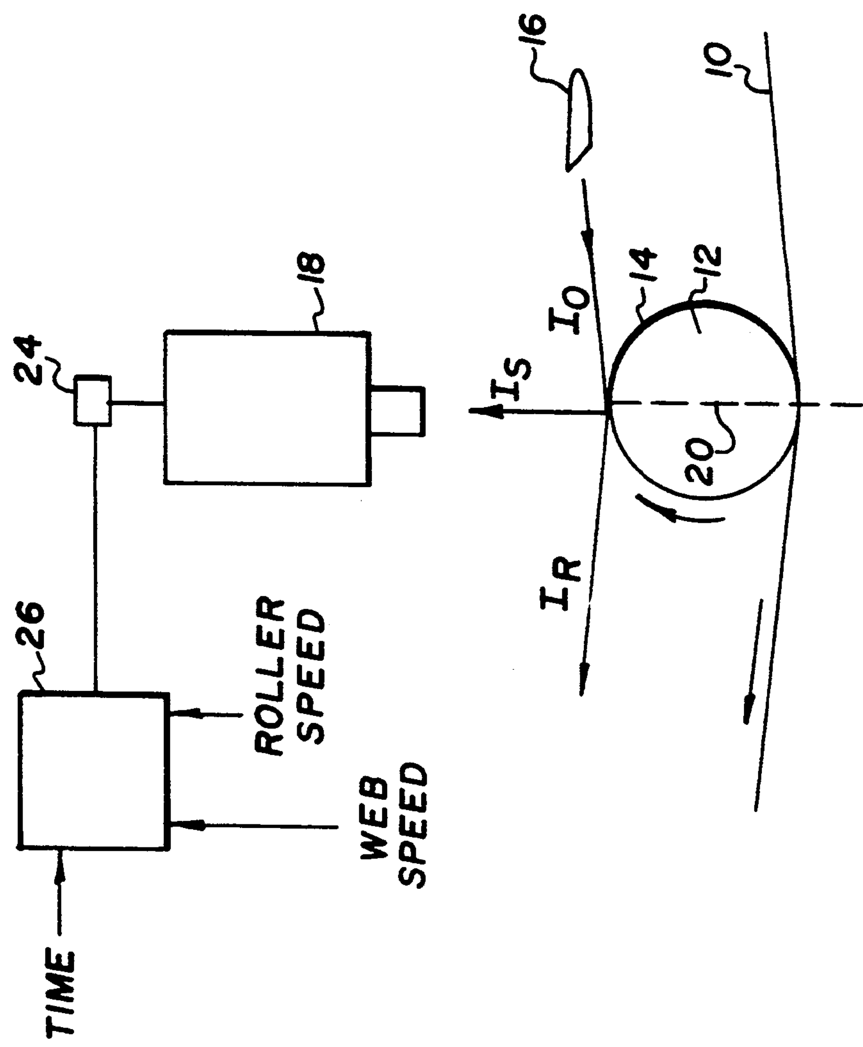
FIG. 1 is a schematic view of an apparatus according to the invention for measurement of particulate contamination on a moving web by sensing on-line the particulate buildup on a particle transfer roller during cleaning of the web.

FIG. 1 illustrates an apparatus according to the invention for measuring the level of particulate contamination on a moving web. Web 10 is moving in the direction indicated in FIG. 1. Means for contacting and removing particles from web 10 is particle transfer roller 12, which is free to rotate in the direction indicated, the rotation being imparted to transfer roller 12 by contact with web 10. Optionally, an idler or backing roller (not shown) can be positioned to form a nip with transfer roller 12 against web 10. Transfer roller 12 has particle-collecting surface 14 thereon. Surface 14 comprises an adhesive or a tacky material having a greater coefficient of adhesion for particles than web 10. The choice of material for surface 14 therefore depends on the coefficient of adhesion of the type of web being cleaned. For example, if web 10 is an acetate or polyester photographic film support, transfer roller 12 can be a polyurethane with sufficient tackiness to lift particles from web 10 upon contact with surface 14 and without having an adhesive placed on surface 14. Typically, polyurethane having a durometer in the range of from about 10 to about 40 Shore A provides the appropriate tackiness and coefficient of adhesion.

Light source 16 is positioned to direct a beam of light of intensity $I_0$ as shown in FIG. 1 against surface 14 of transfer roller 12. Means for sensing the intensity of light reflected from surface (14) and for generating a signal (R) representative of the reflected light intensity is sensor 18. "Light" as used herein includes any wavelength in the electromagnetic spectrum, visible or non-visible, that is within the operational wavelength of a light source/sensor pair, such as light in the infrared wavelength band. Sensor 18 can comprise a photoelectric cell such as a contrast cell or other suitable light sensor, the choice of which can depend on the application, the required sensitivity, and on the type of light source 16. A sensor 18 useful in sensing light originating from a high intensity infrared LED light source 16 is the Smart-Eye SAL, a contrast type of photoelectric cell manufactured by Tri-Tronics Co., Inc. Examples of other useful sensors include a charge coupled device (CCD) and a photomultiplier tube (PMT). A CCD, such as the Veredus, can, in addition to generating a signal representative of contaminant level on the web, also count, size, and classify the particles, as further described below.

As shown in FIG. 1, sensor 18 is positioned to scan a discrete portion or track of surface 14. The use of multiple sensors (18) to scan multiple tracks of transfer roller 12 is also within the scope of the present invention. In this manner, critical zones of surface 14 can be scanned, and the full width of surface 14 can be scanned if desired. The sensors' output signal R can be processed in a manner compatible with the application and environment. For example, different sensor signals R can be processed according to different action limits or geometries (further discussed below) according to factors such as desired zone sensitivity and the like. A programmable logic controller can be employed to carry out such functions.

The inspection geometry of light source 16 and sensor 18 relative to transfer roller 12 can affect the sensitivity of the signal generated by sensor 18 in response to a given amount of particulate loading on surface 14. For example, sensor 18 and light source 16 can be positioned to lie in a plane normal to surface 14 and normal to the axis of transfer roller 12, although any suitable positioning compatible with the application can be chosen. FIG. 1, furthermore, shows what is termed a "dark field" reflection geometry, in which sensor 18 is positioned along the major radial axis 20 of transfer roller 12 intersecting the zone of contact of transfer roller 12 with web 10. Sensor 18 is therefore outside the angle of reflection of light directed from light source 16 reflecting off surface 14, and is positioned to sense scattered light of intensity $I_S$ from surface 14 rather than the reflected light of intensity $I_R$.

Figure 4:
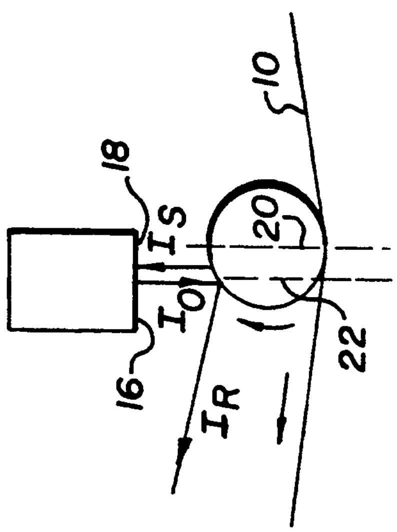
FIG. 4 illustrates apparatus as in FIG. 3 but with the sensor and light source positioned along a minor transfer roller axis.
Figure 3:
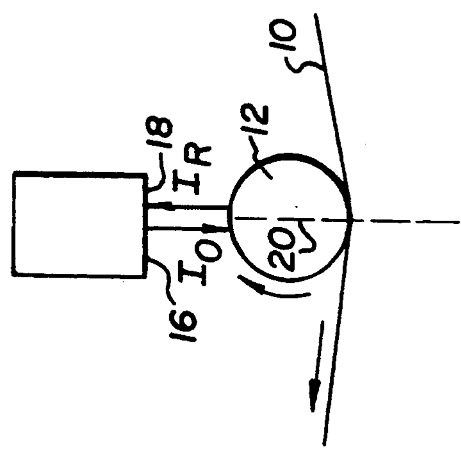
FIG. 3 illustrates apparatus according to the invention in a light field geometry with both the light source and sensor positioned on or near the transfer roller major radial axis.
Figure 2:
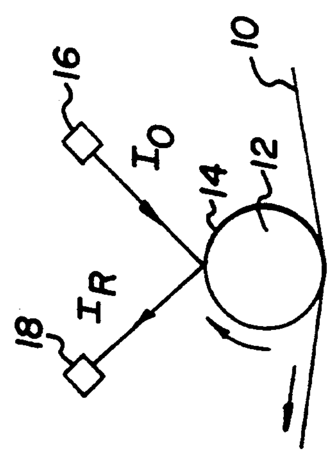
FIG. 2 illustrates apparatus according to the invention in a light field geometry configuration.

The reflection geometry can also comprise a "light field" geometry, shown in FIG. 2. Sensor 18 and light source 16 are each positioned so that sensor 18 receives the light of intensity $I_R$ reflected directly from surface 14. In other words, sensor 18 is positioned at the angle of reflection of light from light source 16 off of surface 14 to sense reflected light of intensity $I_R$. FIG. 3 shows another such light field geometry but with sensor 18 and light source 16 both positioned within the angle of reflection of light from surface 14 and on or close to axis 20. Another light field geometry is termed "off-normal" and is shown in FIG. 4. Both light source 16 and sensor 18 are positioned along a minor axis 22 that is parallel to axis 20. The choice of any of the above geometries can depend on the particular web-cleaning application and environment, the selection of which can be made by initially testing each geometry and without requiring undue experimentation, as will be further evident from the Examples below.

Background light reflecting from surface 14 is sensed by sensor 18 which generates a signal $R_B$ representative of the initial reflected background light intensity, essentially a baseline. Light source 16 is set at a desired intensity level and the beam of light directed at an initially clean surface 14, the reflected light intensity being sensed by sensor 18. Sensor 18 in response generates a signal $R_0$ representative of the initial reflected light intensity and background contribution $R_B$ prior to particle collection by surface 14. $R_0$ can be compensated for or subtracted out by any conventional means, such as by adjusting the intensity of light from light source 16 or by setting sensor output signal at a level subtractive of the $R_0$ contribution. An example of the latter adjustment is to adjust a potentiometer setting on sensor 18 so as to zero $R_0$. As particles are collected by surface 14, sensor 18 receives and senses a different intensity of light. In the dark field geometry configuration of FIG. 1, as particles accumulate on surface 14, the particles scatter light from light source 16 to decrease $I_R$ and increase $I_S$. Sensor 18 in response generates a signal $R_f$ representative of the reflected light intensity $I_S$. As used herein, the term "$R_f$" includes any such signal obtained upon surface 14 collecting particles and not just the last such value of $R_f$, that is, $R_f$ includes any intermediate signals generated by sensor 18 during particle collection. Due to the varying surface character of surface 14, the rotation of transfer roller 12 causes variations in reflected light received by the sensor, with all else being constant. This results in background noise affecting $R_f$ and $R_0$. Means for decreasing or eliminating the background noise component, such as low pass filter 24, can be provided.

As surface 14 accumulates more particles, $R_f$ changes. Means for indicating the difference between $R_0$ and $R_f$ can comprise means for automatically processing the signals, a standard meter or meters for providing a visual indication of each signal, or other such apparatus. In a preferred embodiment, means for indicating the difference between $R_0$ and $R_f$ comprises a means for comparing $R_0$ and $R_f$ and for providing an output signal representative of particulate contamination on the web, such as programmable logic controller 26. Controller 26 can be programmed to provide a time study or graph of particle accumulation on surface 14 representative of the level of particulate contamination on web 10. Controller 26 can also be programmed to calculate, based on web speed, the speed of rotation of transfer roller 12, and other parameters, a value for the level of particle contamination on the web. Controller 26 can further be programmed to track the location and amount of particle contamination on the web. The output signal from controller 26, in addition to providing such values and web locations, can be used in any number of ways to provide the operator with such information or to automatically carry out certain desired operations, such as controlling the speed of web 10 or stopping web 10. Controller 26 can also be used in conjunction with particle transfer roller renewal apparatus to prompt for and/or control the cleaning or servicing of transfer roller 12.

Figure 5:
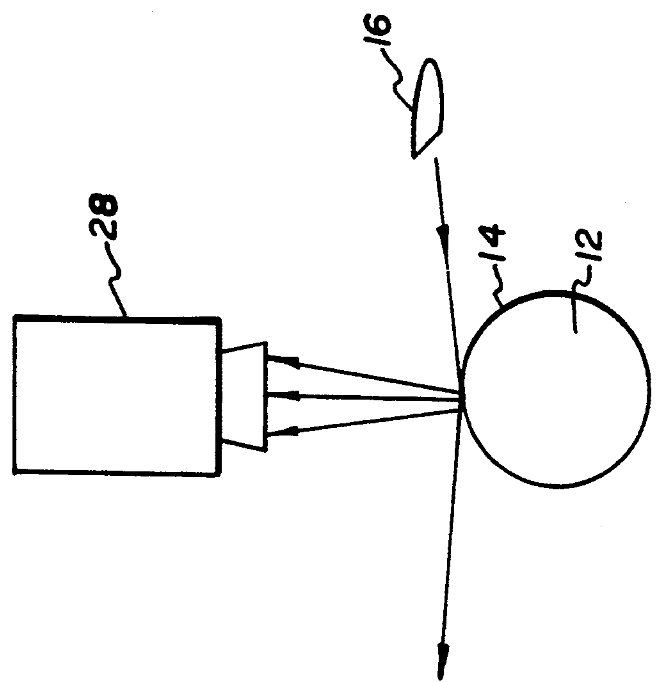
FIG. 5 is a schematic view showing an off-line particle counting and sizing apparatus useful with the apparatus shown in FIG. 1.

FIG. 5 illustrates a preferred embodiment in which the apparatus of the invention includes a Veredus linear CCD array camera 28 as means for counting and sizing the particles collected by the particle-collecting surface. Although FIG. 5 shows off-line apparatus, means for counting and sizing the particles can readily be positioned on-line along with apparatus as illustrated in FIG. 1. Means for counting and sizing should be compatible with the operating roller speed or the transfer roller 12 should be disengaged from cleaning contact with web 10 and operated at a speed compatible with the means for counting and sizing speed capability. As described above, if sensor 28 is a CCD or a PMT, it can itself also serve as means for classifying the particles in addition to counting and sizing particles. "Classification" is a term meaning the determination of the type of particle or roller defect through the analysis of a number of factors, such as particle or defect size, shape, perimeter, area, and color.

The invention will be further illustrated by the following examples of its practise.

EXAMPLE 1

Tests were run using the apparatus shown in FIGS. 1–4 but without the web by using a particle transfer roller already having a contaminant loading. The particle transfer roller used was a matte finish polyurethane roller manufactured by Winfield Industries. The contamination on the roller was slit edge acetate debris generated by the conveyance of a photographic film support web of tricellulose acetate over the roller. The light source was a high intensity infrared LED source with a 780 nm wavelength. The selected wavelength is appropriate, due to its nonphotoreactivity with, a photosensitive environment such as is present in film sensitizing or film-sensitive manufacturing operations. The sensor used was an SAL Smart-Eye manufactured by Tri-Tronics Co., Inc., and the different light focusing devices used were fiber optic bundle models FA-36, FC-36, BFA-36, BFC-36, and BFP-36, and the 01, 02, and V1 lens blocks models. The results for the different geometries are shown in Table I. "Off normal" describes inspection geometry as shown by axis 22 in FIG. 4 for a light field geometry.

TABLE I

| Sensor | Beam Shape | Geometry | Output Signal |
|---|---|---|---|
| FA 36 | Spot 0.125" diameter | Dark field | 1.1 V |
| FC 36 | Linear 0.5" | Dark field | 0.9 V |
| BFA 36 | Spot 0.125" | Light field, off normal | 0.6 V |
| BFC 36 | Linear 0.5" | Light field, off normal | 0.5 |
| BFC 36 | Linear 1.5" | Light field, off normal | 0.2 V |
| 01 | Long range | Light field, off normal | 0.2 V |
| 02 | Short range | Light field, off normal | 0.3 V |
| V1 | Focused short range | Light field, off normal | 0.8 V |

The results show that the most sensitive geometry tested was the dark field using the FA-36 spot fiber optic bundles, providing an output signal of 1.1 V.

EXAMPLE 2

Additional tests were run using a light field, off normal geometry due to its simplicity and relatively good response. The particle transfer roller had a matte finish. 2000 feet of 35 mm tricellulose acetate film were conveyed over an edge guide to produce an accelerated loading condition, and the film was then cleaned by the particle transfer roller. The results demonstrated that a buildup of contamination on the roller from a level of zero to a maximum loading produces an increase in output voltage of 8.4 V from the initial voltage of 0.8 V.

The apparatus and method of the invention are useful in most web-cleaning operations, and particularly those requiring low web contamination levels. The invention provides the ability to gain real-time feedback on web contamination levels and to control the contaminant level on the web and on the means used for cleaning the web. The invention is also useful in identifying a contaminant and a source of contamination. The invention is therefore useful in applications such as the manufacture of paper, photographic films, and other applications requiring the surface cleaning of a web.

The invention has been described in detail with particular reference to preferred embodiments thereof, but it will be understood that variations and modifications can be affected within the spirit and the scope of the invention.

We claim:

1. In a web-cleaning system having means for contacting and removing particles from the web and wherein the means for contacting and removing particles has a particle-collecting surface thereon, an apparatus for measuring particulate contamination transferred from the web to the particle collecting surface characterized by:

a light source positioned to direct a light beam against the particle-collecting surface;

means for sensing the intensity of light reflected from the particle collecting surface and for generating a signal $R_0$ representative of an initial reflected light intensity prior to particle collection by the particle collecting surface and a signal $R_f$ representative of a reflected light intensity after particle collection by the particle collecting surface, the difference between $R_0$ and $R_f$ being a measure of the particulate contamination level transferred from the web to the particle collecting surface; and means for indicating the difference between $R_0$ and $R_f$.

2. The apparatus of claim 1, further comprising means for decreasing or eliminating background noise from signals $R_0$ and $R_f$.

3. The apparatus of claim 1, wherein the means for indicating the difference between $R_0$ and $R_f$ comprises a means for comparing $R_0$ and $R_f$ and for providing an output signal representative of the level of particulate contamination on the web.

4. The apparatus of claim 3, wherein the means for comparing $R_0$ and $R_f$ and for providing an output signal is a programmable logic controller.

5. The apparatus of claim 1, further comprising means for counting and sizing the particles collected by the particle-collecting surface.

6. The apparatus of claim 1, wherein the web is a photographic film.

7. The apparatus of claim 1, wherein the means for contacting and removing particles is a particle transfer roller.

8. A method of measuring particulate contamination transferred from a web to a particle collecting surface in a web-cleaning system, the web-cleaning system having means for contacting and removing particles from the web and wherein the means for contacting and removing particles has said particle-collecting surface thereon, characterized by the steps of:

(a) providing a light source;

(b) providing a means for sensing light intensity and for generating a signal representative of the sensed light intensity;

(c) positioning the light source to direct light therefrom against the particle-collecting surface;

(d) sensing the initial intensity of light reflected from the particle-collecting surface prior to transferring particles from the web to the particle-collecting surface and generating a signal $R_0$ representative of an initial intensity;

(e) contacting the web with the particle-collecting surface to transfer particles from the web to the particle-collecting surface;

(f) sensing a final intensity of light reflected from the particle-collecting surface after transferring particles from the web to the particle-collecting surface and generating a signal $R_f$ representative of the final intensity;

(g) comparing $R_f$ to $R_0$ to obtain a measure of the particulate contamination transferred from the web to the particle collecting surface.

9. The method of claim 8, further comprising the step of counting and sizing the particles collected by the particle-collecting surface.

10. The method of claim 8, wherein the method is carried out on-line with a continuously moving web.

11. The method of claim 10, further comprising the step of decreasing or eliminating background noise from $R_f$ and $R_0$.

12. The method of claim 11, wherein the rate of change of $R_f$ with respect to $R_0$ is monitored to determine relative differences in the amount of particulate contamination on different sections of the web.

13. The method of claim 12, wherein the web is a photographic film.

14. The method of claim 13, wherein the means for contacting and removing particles is a particle transfer roller.

* * * * *